US00PP26825P2

(12) United States Plant Patent
Shoji

(10) Patent No.: US PP26,825 P2
(45) Date of Patent: Jun. 14, 2016

(54) *HYDRANGEA* PLANT NAMED 'B-001'

(50) Latin Name: *Hydrangea macrophylla*
Varietal Denomination: B-001

(71) Applicant: Sakamoto Shoji, Gumma-Ken (JP)

(72) Inventor: Sakamoto Shoji, Gumma-Ken (JP)

( * ) Notice: Subject to any disclaimer, the term of this patent is extended or adjusted under 35 U.S.C. 154(b) by 118 days.

(21) Appl. No.: 14/121,483

(22) Filed: Sep. 10, 2014

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla*, 'B-001', that is characterized by its compact and freely flowering plant habit, its numerous basal branches, its large double sterile flowers that are pure white in color, its leaves that are dark green in color, and its resistance to powdery mildew.

2 Drawing Sheets

Botanical classification: *Hydrangea macrophylla.*
Varietal denomination: 'B-001'.

BACKGROUND OF THE INVENTION

The present invention relates to a new and distinct cultivar of *Hydrangea macrophylla* and will be referred to hereafter by its cultivar name, 'B-001'. 'B-001' represents a new lace-cap type *Hydrangea*, a deciduous shrub grown for landscape use and for use as a potted plant.

The new cultivar is the result of a controlled breeding program conducted by the Inventor in Kurohonemura, Gunma Prefecture, Japan. The new cultivar arose from a cross made in 2008 between unnamed proprietary plants in the Inventor's breeding program; reference no. W-4 as the female parent and reference no. W-3 as the male parent. 'B-001' was selected as single unique plant in 2010.

Asexual reproduction of the new cultivar was first accomplished by the Inventor by softwood stem cuttings in 2010 in Gunma, Japan. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'B-001' as a unique cultivar of *Hydrangea macrophylla.*

1. 'B-001' exhibits a compact and freely flowering plant habit.
2. 'B-001' exhibits numerous basal branches.
3. 'B-001' exhibits large double sterile flowers that are pure white in color.
4. 'B-001' exhibits leaves that are dark green in color.
5. 'B-001' exhibits resistance to powdery mildew.

'W-4', the female parent of 'B-001', differs from 'B-001' in being more susceptible to mildew and in having leaf margins that are more triangular. 'W-3', the male parent of 'B-001', differs from 'B-001' in having single sterile flowers and in having leaves that are larger in size. 'B-001' can be most closely compared to the cultivars 'Hanabi' (not patented) and 'Dancing Snow' (U.S. Plant Pat. No. 21,052). Both are similar to 'B-001' in having double sterile flowers that are white in color and in having leaves that are dark green in color. 'Hanabi' differs from 'B-001' in having a less compact plant habit, in having less compact flowering stems, and in being less floriferous with fewer flowers per inflorescence. 'Dancing Snow' differs from 'B-001' in having more fertile flowers that are more visible in the center of the inflorescences and sterile flowers that are smaller in size.

BRIEF DESCRIPTION OF THE DRAWINGS

The accompanying colored photographs illustrate the overall appearance and distinct characteristics of the new *Hydrangea*. The photographs were taken of a 2 year-old plant as grown in a greenhouse in a 5-liter container in De Kwakel, The Netherlands.

The photograph in FIG. 1 provides a side view of the overall plant habit of 'B-001' in bloom.

Figure 1:
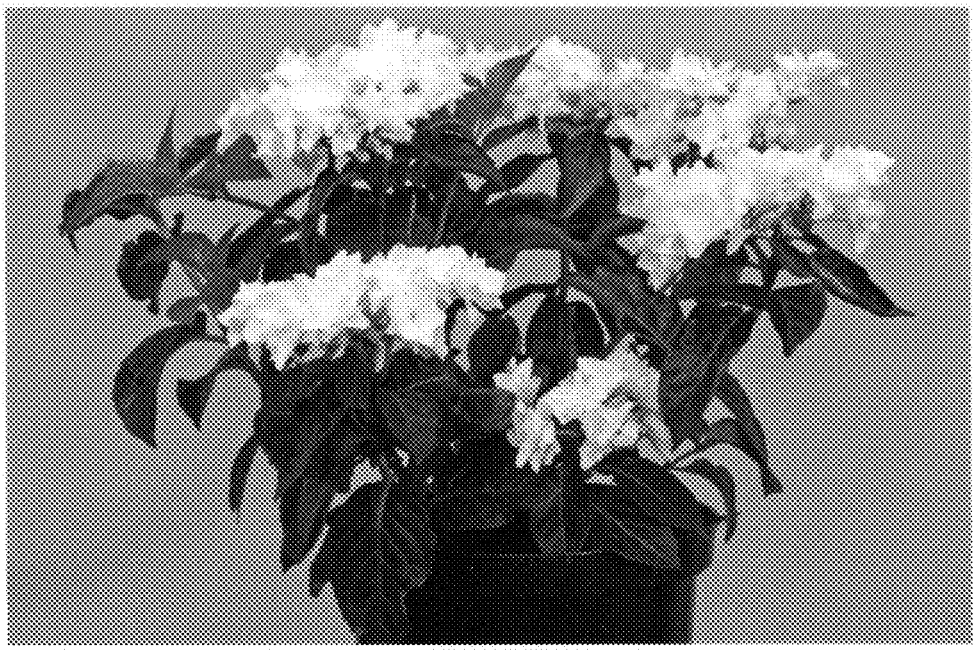
Figure 2:
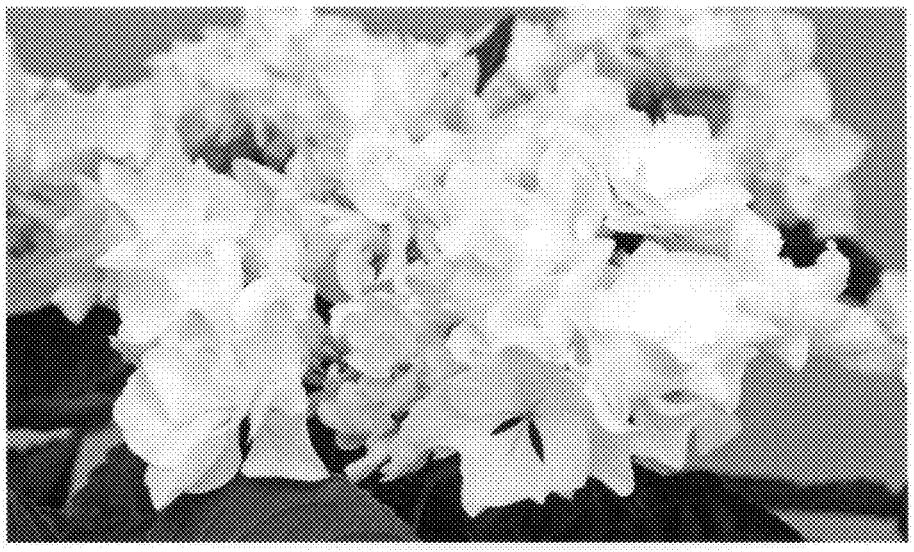

The photograph in FIG. 2 provides a close-up view of an inflorescence of 'B-001'.

Figure 3:
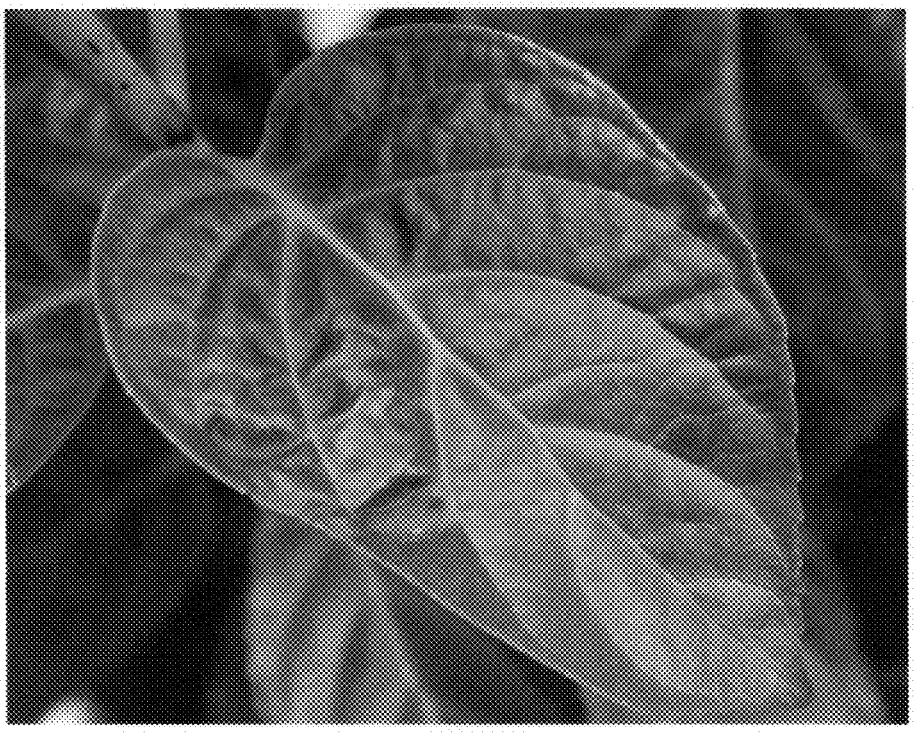

The photograph in FIG. 3 provides a close-up view of a leaf of 'B-001'.

The colors in the photographs are as close as possible with the digital photographic and printing techniques utilized and the color codes in the detailed botanical description accurately describe the new *Hydrangea.*

BOTANICAL DESCRIPTION OF THE PLANT

The following is a detailed description of two year-old plants of 'B-001' as grown in in 5-liter containers in De Kwakel, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—June to September.

*Plant type.*—Deciduous shrub, lacecap type *Hydrangea.*

*Plant habit.*—Compact.

*Height and spread.*—An average of 60 cm in height and 80 cm in width.

*Hardiness.*—At least in U.S.D.A. Zones 5 to 9.

*Diseases resistance.*—Has been observed to have resistance to mildew under the conditions grown.

*Root description.*—Fine.

*Propagation.*—Softwood stem cuttings.

*Growth rate and vigor.*—Moderate.

Stem description:

*Stem shape.*—Round, solid.

*Stem strength.*—Strong.

*Stem color.*—Young growth; 144A, very slightly tinged N186C, mature growth; 199C to 199D.

*Stem size.*—Up to 17.2 cm (excluding inflorescence), average of 5 mm in diameter.

*Stem surface.*—Glabrous.

*Internode length.*—Average of 4.8 cm.

*Branching.*—An average of 14 basal branches, held upright and to an average angle of 45° to soil level.

*Lenticels.*—Stems sparsely covered, average of 0.5 per squared cm, average of 2 mm in length and 1 mm in width and N186C in color.

Foliage description:

*Leaf shape.*—Ovate.

*Leaf arrangement.*—Opposite.

*Leaf division.*—Simple.

*Leaf base.*—Obtuse to very short attenuate.

*Leaf apex.*—Apiculate.

*Leaf margins.*—Serrate (not deeply).

*Leaf venation.*—Pinnate, upper surface color; 144A, lower surface color; 138B.

*Leaf size.*—An average of 9.6 cm in length and 6.1 cm in width.

*Leaf attachment.*—Petiolate.

*Leaf surface.*—Upper surface glabrous, moderately glossy and slightly rugose, lower surface smooth and very slightly glossy.

*Leaf color.*—Young upper surface; between 137B and 143A, young lower surface; 146B, mature upper surface; a color between N137A and 147A, mature lower surface; 147B.

*Petioles.*—Average of 1.5 cm in length and 3 mm in diameter, 144A to 144B in color, glabrous and moderately glossy surface.

Inflorescence description:

*Inflorescence type.*—Terminal compound corymb, lacecap in form, comprised of sterile flowers rising above fertile flowers.

*Lastingness of inflorescence.*—Persistent but color is retained for about 3 to 4 weeks.

*Inflorescence number.*—One per lateral or sublateral stem if pinched.

*Inflorescence size.*—Average of 8.9 cm in height and 17.6 cm in width.

*Flower number.*—Average of 25 sterile flowers and 165 fertile flowers per corymb.

*Flower fragrance.*—None.

*Flower aspect.*—Sterile flowers; upright to slightly outward, fertile flowers; held upright.

*Flower size.*—Sterile flowers; average of 5.3 cm in diameter and 2.4 cm in depth, fertile flowers; average of 2.2 cm in diameter and 2.3 cm in depth.

*Flower type.*—Rotate.

*Flower buds.*—Sterile flowers; average of 1.1 cm in length and 5 mm in diameter, obovate in shape, color is 145D and 145C at the tip, fertile flowers; average of 8 mm in length and 5 mm in diameter, obovate in shape, color is NN155A and 144C at apex.

*Pedicels.*—Sterile flowers; held at an average angle of 30° to main peduncle, average of 2.4 cm in length and 2 mm in width, strong, matte and glabrous surface, 155C in color, fertile flowers; average of 4 mm in length and 1 mm in diameter, held at an average angle of 20° to vertical, moderate strength, surface is matte and smooth, color is 144C, base tinged 166A.

*Petals.*—Sterile flowers; none, fertile flowers; average of 6, rotate in arrangement, deltoid to obovate in shape, entire margin, broad bluntly acute apex, cuneate base, average of 1.6 cm in length and 1.1 cm in width, upper surface glabrous, matte and moderately velvety, lower surface glabrous, matte and slightly velvety, when opening upper and lower surface; 155C, when fully open upper and lower surface; NN155D.

*Sepals.*—Sterile flowers; average of 10, broadly rhomboidal to reniform in shape, an average of 2.4 cm in length and 2 cm in width, bluntly acute apex, broadly cuneate base, upper surface glabrous, matte and moderately velvety, lower surface glabrous, matte and slightly velvety, undulating margins, color when opening upper and lower surface; 155C, color when fully open upper and lower surface; NN155D, fertile flowers; average of 5, obovate in shape, entire margins, acute apex, broad cuneate base, average of 3.5 mm in length and 1.5 mm in width, both surfaces glabrous and matte, color upper and lower surface when opening; 145D with apex 145B, color upper and lower surface when fully open; 155C with apex 145C to 145D.

Reproductive organs:

*Stamens.*—Sterile and fertile flowers; no androecium present.

*Pistils.*—Fertile flowers and on some sterile flowers; average of 3, average of 1 mm in length, stigma is club-shaped and N155B in color, style is an average of 0.6 mm in length and 144B to 144C in color, ovary is 144C in color.

*Fruit and seed.*—No fruit or seed observed to date.

It is claimed:

1. A new and distinct cultivar of *Hydrangea* plant named 'B-001' substantially as herein illustrated and described.

* * * * *